US012116407B2

(12) United States Patent
Hsieh et al.

(10) Patent No.: US 12,116,407 B2
(45) Date of Patent: *Oct. 15, 2024

(54) METHODS OF TREATING NEURODEGENERATIVE DISEASES

(71) Applicant: Academia Sinica, Taipei (TW)

(72) Inventors: Shie-Liang Hsieh, Taipei (TW);
Pei-Shan Sung, Taipei (TW);
Ming-Ting Huang, Taipei (TW);
An-Suei Yang, Emeryville, CA (US);
Chung-Ming Yu, Taipei (TW)

(73) Assignee: Academia Sinica, Taipei (TW)

( * ) Notice: Subject to any disclaimer, the term of this patent is extended or adjusted under 35 U.S.C. 154(b) by 256 days.

This patent is subject to a terminal disclaimer.

(21) Appl. No.: 17/269,991

(22) PCT Filed: Sep. 25, 2019

(86) PCT No.: PCT/US2019/053042
§ 371 (c)(1),
(2) Date: Feb. 19, 2021

(87) PCT Pub. No.: WO2020/069050
PCT Pub. Date: Apr. 2, 2020

(65) Prior Publication Data
US 2022/0213188 A1    Jul. 7, 2022

(51) Int. Cl.
*C07K 16/28* (2006.01)
*A61K 39/00* (2006.01)
*A61P 25/28* (2006.01)
*A61P 31/20* (2006.01)

(52) U.S. Cl.
CPC .......... *C07K 16/2803* (2013.01); *A61P 25/28* (2018.01); *A61P 31/20* (2018.01); *A61K 2039/505* (2013.01); *C07K 2317/56* (2013.01); *C07K 2317/76* (2013.01); *C07K 2317/77* (2013.01)

(58) Field of Classification Search
CPC ............ C07K 16/2803; C07K 2317/56; C07K 2317/76; C07K 2317/77; A61P 25/28; A61P 31/20; A61K 2039/505
See application file for complete search history.

(56) References Cited

U.S. PATENT DOCUMENTS

2019/0002560 A1* 1/2019 Monroe .............. A61K 39/3955
2021/0292413 A1* 9/2021 Hsieh ...................... A61P 25/28

OTHER PUBLICATIONS

Griciuc et al. Alzheimer's Disease risk gene CD3 inhibits microglial uptake of amylloid beta. Neuron, 78: 631-643, 2013. (Year: 2013).*
Yu et al. Developing Therapeutic Antibodies for Neurodegenerative Disease. Neurotherapeutics 10, 459-472 (2013). (Year: 2013).*

* cited by examiner

*Primary Examiner* — Julie Wu
*Assistant Examiner* — Amber K Faust
(74) *Attorney, Agent, or Firm* — NZ CARR LAW OFFICE

(57) ABSTRACT

Provided herein is a method for treating neurodegenerative diseases, such as Alzheimer's disease (AD), by use of monoclonal antibody, which exhibits a binding affinity to Siglec-3 receptor. According to some embodiments of the present disclosure, the monoclonal antibody is capable of enhancing phagocytosis of neurotoxic peptides by immune cells thereby providing a neuroprotective effect to a subject in need thereof.

4 Claims, 3 Drawing Sheets
Specification includes a Sequence Listing.

SEQUENCE LISTING

<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: synthesized-CDR-L2

<400> SEQUENCE: 1

Ile Ser Ser Ala Gly
1               5

<210> SEQ ID NO 2
<211> LENGTH: 6
<212> TYPE: PRT
<213> ORGANISM: Artificial Sequence
<220> FEATURE:
<223> OTHER INFORMATION: synthesized-CDR-L3

<400> SEQUENCE: 2

Gln Tyr Phe Asn Phe Pro
1               5

<210> SEQ ID NO 3
<211> LENGTH: 4
<212> TYPE: PRT
<213> ORGANISM: Artificial Sequence
<220> FEATURE:
<223> OTHER INFORMATION: synthesized-CDR-H1

<400> SEQUENCE: 3

Asn Asn Gly Trp
1

<210> SEQ ID NO 4
<211> LENGTH: 10
<212> TYPE: PRT
<213> ORGANISM: Artificial Sequence
<220> FEATURE:
<223> OTHER INFORMATION: synthesized-CDR-H2

<400> SEQUENCE: 4

Gly Ile Gly Pro Tyr Gly Gly Ser Thr Phe
1               5                   10

<210> SEQ ID NO 5
<211> LENGTH: 10
<212> TYPE: PRT
<213> ORGANISM: Artificial Sequence
<220> FEATURE:
<223> OTHER INFORMATION: synthesized-CDR-H3

<400> SEQUENCE: 5

Ser Arg Phe Ile Gly Ser Tyr Ser His Met
1               5                   10

<210> SEQ ID NO 6
<211> LENGTH: 237
<212> TYPE: PRT
<213> ORGANISM: Artificial Sequence
<220> FEATURE:
<223> OTHER INFORMATION: synthesized-VL region

<400> SEQUENCE: 6

Met Arg Val Pro Ala Gln Leu Leu Gly Leu Leu Leu Leu Trp Leu Pro
1               5                   10                  15

```
Gly Ala Arg Cys Asp Gly Thr Asp Ile Gln Met Thr Gln Ser Pro Ser
            20                  25                  30

Ser Leu Ser Ala Ser Val Gly Asp Arg Val Thr Ile Thr Cys Arg Ala
        35                  40                  45

Ser Gln Asp Val Tyr Tyr Val Ala Trp Tyr Gln Gln Lys Pro Gly
    50                  55                  60

Lys Ala Pro Lys Leu Leu Ile Ser Ser Ala Gly Leu Tyr Ser Gly
65                  70                  75                  80

Val Pro Ser Arg Phe Ser Gly Ser Gly Thr Asp Phe Thr Leu
                85                  90                  95

Thr Ile Ser Ser Leu Gln Pro Glu Asp Phe Ala Thr Tyr Tyr Cys Gln
                100                 105                 110

Gln Tyr Phe Asn Phe Pro Leu Thr Phe Gly Gln Gly Thr Lys Val Glu
            115                 120                 125

Ile Lys Arg Thr Val Ala Ala Pro Ser Val Phe Ile Phe Pro Pro Ser
130                 135                 140

Asp Glu Gln Leu Lys Ser Gly Thr Ala Ser Val Val Cys Leu Leu Asn
145                 150                 155                 160

Asn Phe Tyr Pro Arg Glu Ala Lys Val Gln Trp Lys Val Asp Asn Ala
                165                 170                 175

Leu Gln Ser Gly Asn Ser Gln Glu Ser Val Thr Glu Gln Asp Ser Lys
            180                 185                 190

Asp Ser Thr Tyr Ser Leu Ser Ser Thr Leu Thr Leu Ser Lys Ala Asp
        195                 200                 205

Tyr Glu Lys His Lys Val Tyr Ala Cys Glu Val Thr His Gln Gly Leu
    210                 215                 220

Ser Ser Pro Val Thr Lys Ser Phe Asn Arg Gly Glu Cys
225                 230                 235

<210> SEQ ID NO 7
<211> LENGTH: 468
<212> TYPE: PRT
<213> ORGANISM: Artificial Sequence
<220> FEATURE:
<223> OTHER INFORMATION: synthesized-VH region

<400> SEQUENCE: 7

Met Gly Trp Ser Leu Ile Leu Leu Phe Leu Val Ala Val Ala Thr Arg
1               5                   10                  15

Val Ala Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Thr Ile
        35                  40                  45

Asn Asn Gly Trp Ile His Trp Val Arg Gln Ala Pro Gly Lys Gly Leu
    50                  55                  60

Glu Trp Val Ala Gly Ile Gly Pro Tyr Gly Gly Ser Thr Phe Tyr Ala
65                  70                  75                  80

Asp Ser Val Lys Gly Arg Phe Thr Ile Ser Ala Asp Thr Ser Lys Asn
                85                  90                  95

Thr Ala Tyr Leu Gln Met Asn Ser Leu Arg Ala Glu Asp Thr Ala Val
            100                 105                 110

Tyr Tyr Cys Ser Arg Phe Ile Gly Ser Tyr Ser His Met Asp Tyr Trp
        115                 120                 125

Gly Gln Gly Thr Leu Val Thr Val Ser Ser Ala Ser Thr Lys Gly Pro
130                 135                 140
```

-continued

Ser Val Phe Pro Leu Ala Pro Ser Ser Lys Ser Thr Ser Gly Gly Thr
145                 150             155             160

Ala Ala Leu Gly Cys Leu Val Lys Asp Tyr Phe Pro Glu Pro Val Thr
                165             170             175

Val Ser Trp Asn Ser Gly Ala Leu Thr Ser Gly Val His Thr Phe Pro
            180             185             190

Ala Val Leu Gln Ser Ser Gly Leu Tyr Ser Leu Ser Ser Val Val Thr
        195             200             205

Val Pro Ser Ser Ser Leu Gly Thr Gln Thr Tyr Ile Cys Asn Val Asn
    210             215             220

His Lys Pro Ser Asn Thr Lys Val Asp Lys Lys Ala Glu Pro Lys Ser
225             230             235             240

Cys Asp Lys Thr His Thr Cys Pro Pro Cys Pro Ala Pro Glu Leu Leu
            245             250             255

Gly Gly Pro Ser Val Phe Leu Phe Pro Pro Lys Pro Lys Asp Thr Leu
            260             265             270

Met Ile Ser Arg Thr Pro Glu Val Thr Cys Val Val Val Asp Val Ser
        275             280             285

His Glu Asp Pro Glu Val Lys Phe Asn Trp Tyr Val Asp Gly Val Glu
    290             295             300

Val His Asn Ala Lys Thr Lys Pro Arg Glu Glu Gln Tyr Asn Ser Thr
305             310             315             320

Tyr Arg Val Val Ser Val Leu Thr Val Leu His Gln Asp Trp Leu Asn
            325             330             335

Gly Lys Asp Tyr Lys Cys Lys Val Ser Asn Lys Ala Leu Pro Ala Pro
            340             345             350

Ile Glu Lys Thr Ile Ser Lys Ala Lys Gly Gln Pro Arg Glu Pro Gln
            355             360             365

Val Tyr Thr Leu Pro Pro Ser Arg Asp Glu Leu Thr Arg Asn Gln Val
    370             375             380

Ser Leu Thr Cys Leu Val Lys Gly Phe Tyr Pro Ser Asp Ile Ala Val
385             390             395             400

Glu Trp Glu Ser Asn Gly Gln Pro Glu Asn Asn Tyr Lys Thr Thr Pro
            405             410             415

Pro Val Leu Asp Ser Asp Gly Ser Phe Phe Leu Tyr Ser Lys Leu Thr
            420             425             430

Val Asp Lys Ser Arg Trp Gln Gln Gly Asn Val Phe Ser Cys Ser Val
        435             440             445

Met His Glu Ala Leu His Asn His Tyr Thr Gln Lys Ser Leu Ser Leu
450             455             460

Ser Pro Gly Lys
465

METHODS OF TREATING NEURODEGENERATIVE DISEASES

CROSS-REFERENCE TO RELATED APPLICATION

This application is a U.S. National Stage Filing under 35 U.S.C. 371 from International Patent Application Serial No. PCT/US2019/053042, entitled "METHODS OF TREATING NEURODEGENERATIVE DISEASES," filed on Sep. 25, 2019, and published on Apr. 2, 2020, the disclosure of which are incorporated by reference herein in their entireties.

BACKGROUND OF THE INVENTION

1. Field of the Invention

The present disclosure in general relates to the field of disease treatment. More particularly, the present disclosure relates to uses of an anti-Siglec-3 antibody in the treatment of neurodegenerative diseases.

2. Description of Related Art

Neurodegeneration is a process characterized by progressive and irreversible neuronal damage and death. Many neurological diseases, including amyotrophic lateral sclerosis (ALS), Parkinson's disease (PD), Alzheimer's disease (AD), Huntington's disease (HD), frontotemporal dementia, and spinocerebellar ataxias, are considered be caused by the neurodegenerative process. These diseases are diverse in their pathophysiology, some of which result in memory and cognitive impairments, while others of which affect the ability of movement, speak and breath of patients.

There is no specific treatment for reversing the neurodegenerative process. Although several medicines have been approved by U.S. Food and Drug Administration (FDA), for example, riluzole and edaravone for treating ALS, safinamide for treating PD, and donepezil and galantamine for treating AD, none of these medicines cure neurodegenerative diseases, but only slows the disease progression. Further, it has been reported that neurodegenerative patients may develop tolerance to these medicines during prolonged treatment thereby decreasing the efficacy of treatment.

In view of the foregoing, there exists in the related art a need for a novel method for efficiently treating neurodegenerative diseases so as to improve the life quality and expectancy of patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a use of an antibody for manufacturing a medicament or a pharmaceutical composition for the treatment of a neurodegenerative disease. The medicament or the pharmaceutical composition comprises an effective amount of the antibody, and a pharmaceutically acceptable carrier.

According to embodiments of the present disclosure, the antibody comprises a light chain variable (VL) region and a heavy chain variable (VH) region, in which the VL region comprises a first light chain complementarity determining region (CDR-L1), a second light chain CDR (CDR-L2), and a third light chain CDR (CDR-L3); and the VH region comprises a first heavy chain CDR (CDR-H1), a second heavy chain CDR (CDR-H2), and a third heavy chain CDR (CDR-H3).

According to some embodiments of the present disclosure, the CDR-L1 has the amino acid sequence of VYY, the CDR-L2 has the amino acid sequence of ISSAG (SEQ ID NO: 1), and the CDR-L3 has the amino acid sequence of QYFNFP (SEQ ID NO: 2). In these embodiments, the CDR-H1 has the amino acid sequence of NNGW (SEQ ID NO: 3), the CDR-H2 has the amino acid sequence of GIGPYGGSTF (SEQ ID NO: 4), and the CDR-H3 has the amino acid sequence of SRFIGSYSHM (SEQ ID NO: 5).

Preferably, the VL region of the antibody comprises the amino acid sequence at least 85% identical to SEQ ID NO: 6, and the VH region of the antibody comprises the amino acid sequence at least 85% identical to SEQ ID NO: 7. More preferably, the VL region of the antibody comprises the amino acid sequence at least 90% identical to SEQ ID NO: 6, and the VH region of the antibody comprises the amino acid sequence at least 90% identical to SEQ ID NO: 7. Most preferably, the VL and VH regions of the antibody respectively comprise the amino acid sequences at least 95% identical to SEQ ID NOs: 6 and 7. In one specific example, the VL region of the antibody comprises the amino acid sequence 100% identical to SEQ ID NO: 6, and the VH region of the antibody comprises the amino acid sequence 100% identical to SEQ ID NO: 7.

Also disclosed therein is a method of treating a neurodegenerative disease in a subject. The method comprises administering to the subject an effective amount of the antibody, medicament, or pharmaceutical composition of the present disclosure.

Examples of neurodegenerative disease treatable by the present antibody, medicament, pharmaceutical composition, and/or method include, but are not limited to, amyotrophic lateral sclerosis (ALS), Parkinson's disease (PD), Alzheimer's disease (AD), Huntington's disease (HD), frontotemporal dementia (FTD), spinocerebellar ataxias (SCA), Machado-Joseph disease (MJD), dentatorubral pallidoluysian atrophy (DRPLA), spinal and bulbar muscular atrophy (SBMA), and fragile X-associated tremor and ataxia syndrome (FXTAS). According to certain embodiments of the present disclosure, the neurodegenerative disease is AD.

The subject is preferably a mammal, for example, a human, mouse, rat, guinea pig, hamster, monkey, swine, dog, cat, horse, sheep, goat, cow, or rabbit. More preferably, the subject is a human.

Many of the attendant features and advantages of the present disclosure will become better understood with reference to the following detailed description considered in connection with the accompanying drawings.

BRIEF DESCRIPTION OF THE DRAWINGS

The present description will be better understood from the following detailed description read in light of the accompanying drawings, where.

monocytes treated with phosphate buffered saline (PBS); hIgG1: monocytes treated with human IgG1 isotype antibody; 1008: monocytes treated with mAb 1008; isotype: monocytes stained with isotype control antibodies.

Figure 2A:
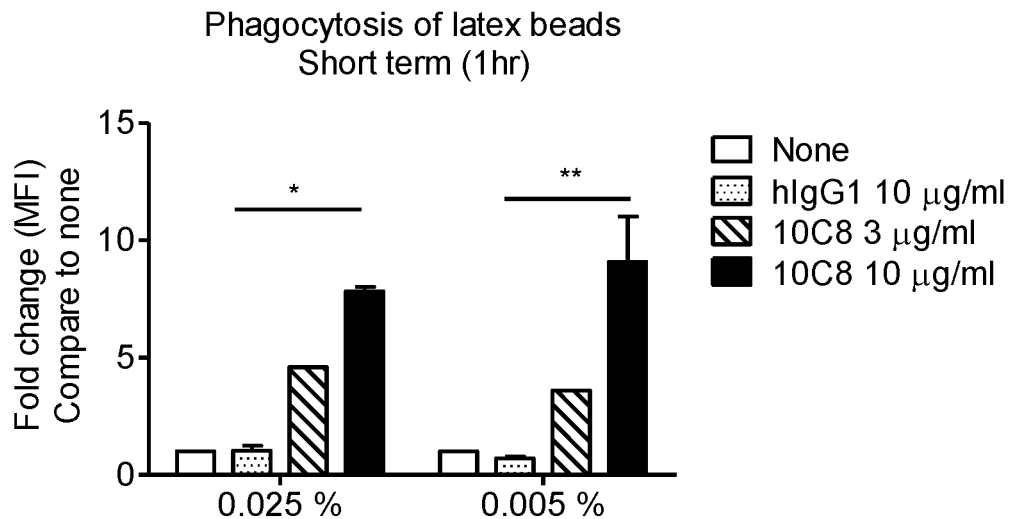
Figure 2B:
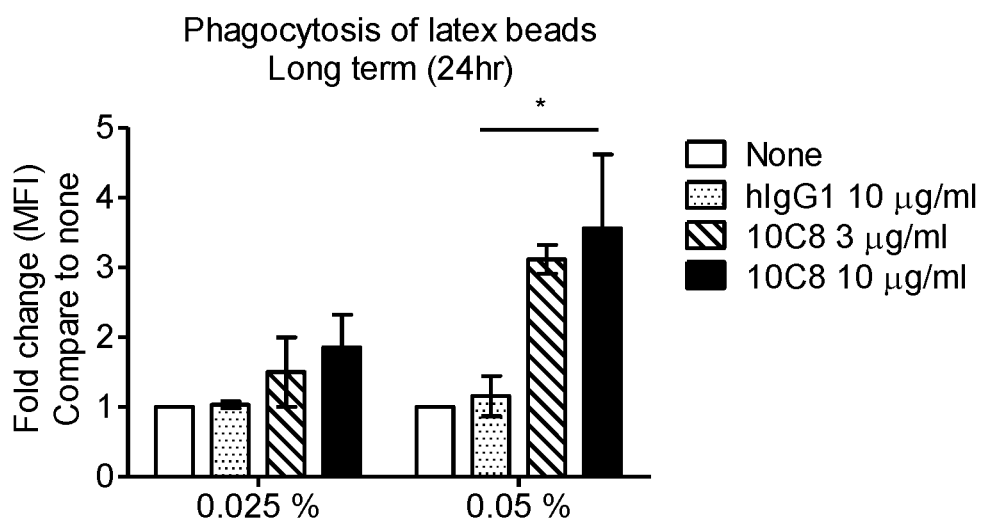

FIGS. 2A and 2B are histograms respectively depicting the fold changes in the mean fluorescence intensity (MFI) of human CD14$^+$ monocytes according to Example 1.2 of the present disclosure, in which the monocytes were administered with specific treatments followed by incubation with 0.025% or 0.05% green fluorescent latex beads. The MFI of monocytes was determined by flow cytometry.

Figure 3A:
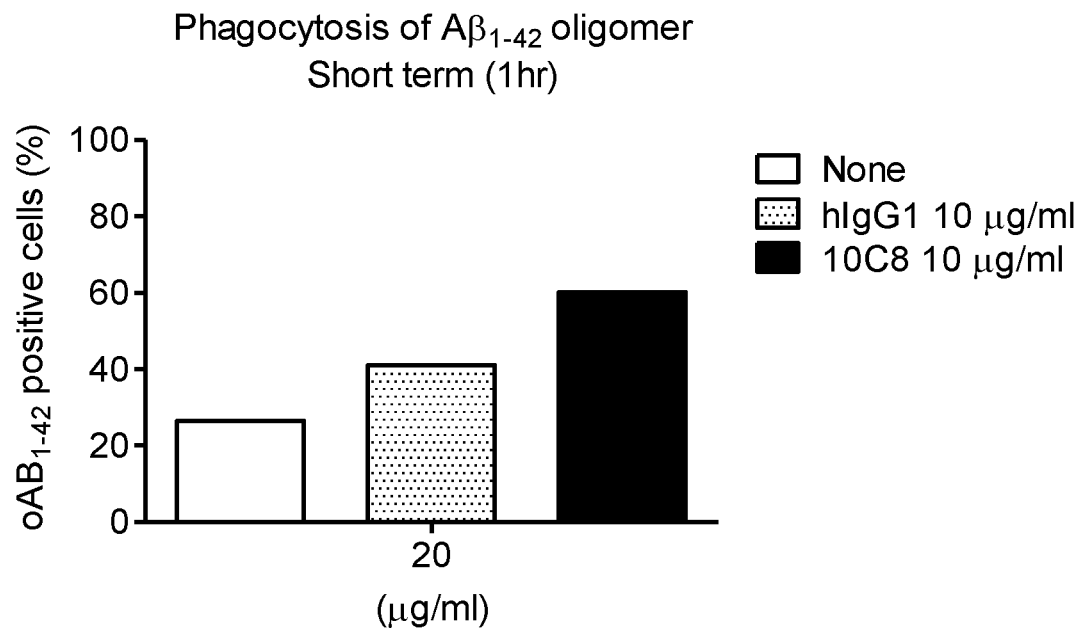
Figure 3B:
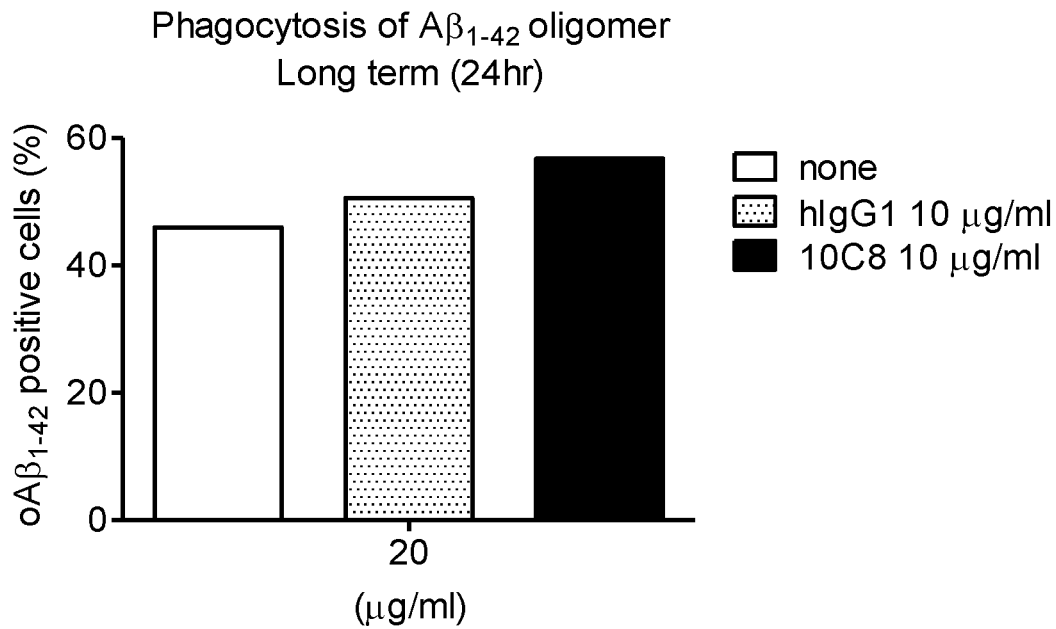

FIGS. 3A and 3B are histograms respectively depicting the percentages of $A\beta_{1-42}$ positive monocytes according to Example 1.2 of the present disclosure, in which human CD14$^+$ monocytes were administered with specific treatments followed by incubation with 20 µg/ml of green fluorescent $A\beta_{1-42}$ peptide. The percentages of monocytes expressing the $A\beta_{1-42}$ peptide were determined by flow cytometry.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here. Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The term "antibody" is used in the broadest sense and specifically covers monoclonal antibodies (including full length monoclonal antibodies), polyclonal antibodies, multi-specific antibodies (e.g., bi-specific antibodies), and antibody fragments so long as they exhibit the desired biological activity. The term "antibody fragment" comprises a portion of a full length antibody, generally the antigen binding or variable region thereof. Examples of antibody fragments include Fab, Fab', F(ab')2, and Fv fragments; diabodies; linear antibodies; single-chain antibody molecules; and multi-specific antibodies formed from antibody fragments.

The "variable region" of an antibody refers to the amino-terminal domains of heavy or light chain of the antibody. These domains are generally the most variable parts of an antibody and contain the antigen-binding sites. The term "variable" refers to the fact that certain portions of the variable regions differ extensively in sequence among antibodies, and are used in the binding and specificity of each particular antibody for its particular antigen. However, the variability is not evenly distributed throughout the variable regions of antibodies. It is concentrated in three segments called complementarity-determining regions (CDRs) or hypervariable regions both in the light-chain and the heavy-chain variable regions. The more highly conserved portions of variable regions are called the framework (FR). The variable regions of native heavy and light chains each comprises four FR regions, largely adopting a beta-sheet configuration, connected by three CDRs, which form loops connecting, and in some cases forming part of, the beta-sheet structure. The CDRs in each chain are held together in close proximity by the FR regions, and with the CDRs from the other chain, contribute to the formation of the antigen-binding site of antibodies. The constant domains are not involved directly in binding an antibody to an antigen, but exhibit various effector functions, such as participation of the antibody in antibody-dependent cellular toxicity.

The term "complementarity determining region" (CDR) used herein refers to the hypervariable region of an antibody molecule that forms a surface complementary to the 3-dimensional surface of a bound antigen. Proceeding from N-terminus to C-terminus, each of the heavy and light chains of the antibody comprises three CDRs (i.e., CDR-H1, CDR-H2, and CDR-H3 in each heavy chain; and CDR-L1, CDR-L2, and CDR-L3 in each light chain). A HLA-DR antigen-binding site, therefore, includes a total of six CDRs that comprise three CDRs from the variable region of a heavy chain and three CDRs from the variable region of a light chain.

Depending on the amino acid sequences of the constant domains of their heavy chains, antibodies (immunoglobulins) can be assigned to different classes. There are five major classes of immunoglobulins: IgA, IgD, IgE, IgG and IgM, and several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. The subunit structures and three-dimensional configurations of different classes of immunoglobulins are well known and described generally in, for example, Abbas et al. Cellular and Mol. Immunology, 4th ed. (2000). An antibody may be part of a larger fusion molecule, formed by covalent or non-covalent association of the antibody with one or more other proteins or peptides.

As discussed herein, minor variations in the amino acid sequences of antibodies are contemplated as being encompassed by the presently disclosed and claimed inventive concept(s), providing that the variations in the amino acid sequence maintain at least 85% sequence identity, such as at least 85%, 86%, 87%, 88%, 89%, 90%, 91%, 92%, 93%, 94%, 95%, 96%, 97%, 98% and 99% sequence identity. Antibodies of the present disclosure may be modified specifically to alter a feature of the peptide unrelated to its physiological activity. For example, certain amino acids can be changed and/or deleted without affecting the physiological activity of the antibody in this study (i.e., its ability to enhance phagocytic activity of immune cells). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy families; asparagine and glutamine are an amide-containing family; alanine, valine, leucine, and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative. Fragments or analogs of antibodies can be readily prepared by those of ordinary skill in the art. Preferred amino- and carboxyl-termini of fragments or analogs occur near boundaries of functional domains. In one example, one amino acid residue (e.g., valine) of the present antibody is conservatively replaced (e.g., by leucine). In other examples, two amino acid residues of the present antibody are conservatively replaced by other suitable amino acid residues, for example, valine (V) and arginine (R) are replaced by the pair of amino acids that includes, but is not limited to, methionine (M) and lysine (K), lysine (K) and proline (P), tryptophan (W) and isoleucine (I), isoleucine (I) and proline (P), asparagine (N) and valine (V), and glutamine (G) and lysine (K).

"Percentage (%) sequence identity" is defined as the percentage of amino acid residues in a candidate sequence that are identical with the amino acid residues in the specific peptide sequence, after aligning the sequences and introducing gaps, if necessary, to achieve the maximum percent sequence identity, and not considering any conservative substitutions as part of the sequence identity. Alignment for purposes of determining percentage sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared. For purposes herein, sequence comparison between two amino acid sequences was carried out by computer program Blastp (protein-protein BLAST) provided online by Nation Center for Biotechnology Information (NCBI). The percentage amino acid sequence identity of a given amino acid sequence A to a given amino acid sequence B (which can alternatively be phrased as a given amino acid sequence A that has a certain % amino acid sequence identity to a given amino acid sequence B) is calculated by the formula as follows:

$$\frac{X}{Y} \times 100$$

where X is the number of amino acid residues scored as identical matches by the sequence alignment program BLAST in that program's alignment of A and B, and where Y is the total number of amino acid residues in A or B, whichever is shorter.

The term "effective amount" as referred to herein designate the quantity of a component which is sufficient to yield a desired response. For therapeutic purposes, the effective amount is also one in which any toxic or detrimental effects of the component are outweighed by the therapeutically beneficial effects. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the structure of the compounds or its derivatives. Effective amount may be expressed, for example, in grams, milligrams or micrograms or as milligrams per kilogram of body weight (mg/Kg). Alternatively, the effective amount can be expressed in the concentration of the active component (e.g., the present antibody), such as molar concentration, mass concentration, volume concentration, molality, mole fraction, mass fraction and mixing ratio. Persons having ordinary skills could calculate the human equivalent dose (HED) for the medicament (such as the present antibody) based on the doses determined from animal models. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

As used herein, the term "treat," "treating" and "treatment" are interchangeable, and encompasses partially or completely preventing, ameliorating, mitigating and/or managing a symptom, a secondary disorder or a condition associated with neurodegenerative diseases. The term "treating" as used herein refers to application or administration of the present antibody to a subject, who has a symptom, a secondary disorder or a condition associated with a neurodegenerative disease, with the purpose to partially or completely alleviate, ameliorate, relieve, delay onset of, inhibit progression of, reduce severity of, and/or reduce incidence of one or more symptoms, secondary disorders or features associated with the neurodegenerative disease. Symptoms, secondary disorders, and/or conditions associated with neurodegenerative diseases include, but are not limited to, memory loss, apathy, anxiety, agitation, mood changes, cognitive decline, slowness of movement, lack of spontaneous motility, resting tremor, rigidity, incoordination, and behavioral disturbance. Treatment may be administered to a subject who exhibits only early signs of such symptoms, disorder, and/or condition for the purpose of decreasing the risk of developing the symptoms, secondary disorders, and/or conditions associated with neurodegenerative diseases. Treatment is generally "effective" if one or more symptoms or clinical markers are reduced as that term is defined herein. Alternatively, a treatment is "effective" if the progression of a symptom, disorder or condition is reduced or halted.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The terms "subject" and "patient" are interchangeably used in the present disclosure, and refer to a mammal including the human species that is treatable with the antibody, medicament, pharmaceutical composition, and/or method of the present invention. The term "subject" is intended to refer to both the male and female gender.

II. Description of the Invention

The accumulation of neurotoxic peptides in neurons is a feature shared by different neurodegenerative diseases. For example, the brains of AD patients are characterized by the presence of extracellular amyloid plaques formed by beta-amyloid (Aβ) peptides; such highly insoluble plaques cause damage to synapses of brain resulting in the memory and cognition impairments of AD patients. The pathological hallmark of PD is the widespread accumulation of cellular deposits (i.e., Lewy bodies) comprised of alpha-synuclein fibrils; the accumulated deposits are known to damage neurons thereby affecting mental capability, behavior, and movement of PD patients. Regarding HD, it has been reported that mutations in IT15 gene lead to an abnormally long polyglutamine (polyQ) expansion in huntingtin (Htt) protein, and the polyQ expansion makes Htt protein prone to aggregate and accumulates in the brain thereby interfering synaptic signaling of HD patients. In view of these neurotoxic peptides playing a critical role in the development and progression of neurodegenerative diseases, there is a need in the art for methods of efficiently eliminating neurotoxic peptides so as to provide a therapeutic effect to a subject in need thereof, e.g., a subject having or suspected of having a neurodegenerative disease, or a subject at risk of having a neurodegenerative disease.

The present disclosure is based, at least in part, on the discovery that an antibody specific to sialic acid-binding immunoglobulin-like lectin-3 (Siglec-3) enhances the phagocytosis of neurotoxic peptides (e.g., AP peptides) by immune cells, and accordingly, is useful in removing neurotoxic peptides from neurons and providing a neuroprotective effect to a subject in need thereof. The present disclosure thus pertains to a monoclonal antibody (mAb) or its fragment, which exhibits binding specificity to Siglec-3, and uses of the mAb or antibody fragment in the preparation of a medicament or a pharmaceutical composition for treating neurodegenerative diseases.

According to embodiments of the present disclosure, the mAb designated as clone 1008 comprises a VL region and a VH region, in which the VL region comprises CDR-L1, CDR-L2, and CDR-L3, and the VH region comprises CDR-H1, CDR-H2 and CDR-H3. According to some embodiments, the CDR-L1, CDR-L2 and CDR-L3 of mAb 1008 respectively have the amino acid sequences of VYY, ISSAG (SEQ ID NO: 1) and QYFNFP (SEQ ID NO: 2), and the CDR-H1, CDR-H2 and CDR-H3 of mAb 1008 respectively have the amino acid sequences of NNGW (SEQ ID NO: 3), GIGPYGGSTF (SEQ ID NO: 4), and SRFIGSYSHM (SEQ ID NO: 5).

According to certain embodiments, the VL region of mAb 1008 comprises the amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 6, and the VH region of mAb 1008 comprises the amino acid sequence at least 85% (i.e., 85%, 86%, 87%, 88%, 89%, 90%, 91%, 92%, 93%, 94%, 95%, 96%, 97%, 98%, 99% or 100%) identical to SEQ ID NO: 7. As could be appreciated, the framework (FR) sequence of the VL and VH regions may vary (e.g., being substituted by conserved or non-conserved amino acid residues) without affecting the binding affinity and/or specificity of the present antibody. Preferably, the sequences of the framework is conservatively substituted by one or more suitable amino acid(s) with similar properties; for example, the substitution of leucine (an nonpolar amino acid residue) by isoleucine, alanine, valine, proline, phenylalanine, or tryptophan (another nonpolar amino acid residue); the substitution of aspartate (an acidic amino acid residue) by glutamate (another acidic amino acid residue); or the substitution of lysine (an basic amino acid residue) by arginine or histidine (another basic amino acid residue). According to preferred embodiments, the VL and VH regions of mAb 1008 respectively comprises the amino acid sequences at least 90% identical to SEQ ID NOs: 6 and 7. More preferably, the VL and VH regions of mAb 1008 respectively comprises the amino acid sequences at least 95% identical to SEQ ID NOs: 6 and 7. In one specific example of the present disclosure, the VL and VH regions of mAb 1008 respectively comprises the amino acid sequences 100% identical to SEQ ID NOs: 6 and 7.

According to some examples of the present disclosure, the present mAb (i.e., mAb 1008) is capable of enhancing the phagocytic activity of immune cells, such as monocytes/macrophages. Compared with IgG control group, the treatment of mAb 1008 increases the uptake of neurotoxic peptide (e.g., Aβ peptide) by immune cells.

Accordingly, a further aspect of the present disclosure is to provide a pharmaceutical composition or medicament, which comprises the present antibody (i.e., mAb 1008) or a fragment thereof; and optionally, a pharmaceutically acceptable carrier.

Generally, the mAb or the antibody fragment of this invention is present at a level of about 0.1% to 99% by weight, based on the total weight of the pharmaceutical composition or medicament. In some embodiments, the mAb or the antibody fragment of this invention is present at a level of at least 1% by weight, based on the total weight of the pharmaceutical composition or medicament. In certain embodiments, the mAb or the antibody fragment is present at a level of at least 5% by weight, based on the total weight of the pharmaceutical composition or medicament. In still other embodiments, the mAb or the antibody fragment is present at a level of at least 10% by weight, based on the total weight of the pharmaceutical composition or medicament. In still yet other embodiments, the mAb or the antibody fragment is present at a level of at least 25% by weight, based on the total weight of the pharmaceutical composition or medicament.

The present pharmaceutical composition or medicament may be formulated into solid, semi-solid, or liquid forms, such as tablets, capsules, powders, granules, solutions, and injections. As such, administration of the present mAb or the antibody fragment can be achieved in various ways, including oral, buccal, parental, intravenous, intraperitoneal, and etc. administration. In pharmaceutical dosage forms, the present mAb or the antibody fragment may be administered alone or in combination with other known pharmaceutically active agent to treat neurodegenerative diseases. One of skilled person in the art is familiar with the various dosage forms that are suitable for use in each route. It is to be noted that the most suitable route in any given case would depend on the nature or severity of the disease or condition being treated.

Applicable solid carriers may include one or more substances that may act as flavoring agent, lubricant, solubilizer, suspending agent, filler, glidant, compression aid, binder or tablet-disintegrating agent or an encapsulating material. In powders, the carrier is a finely divided solid that is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carrier includes, for example, calcium phosphate, magnesium stearate, talc, sugars, lactose, dextrin, starch, gelatin, cellulose, methylcellulose, sodium carboxymethyl cellulose, polyvinyl pyrrolidine and the like.

The mAb or the antibody fragment of the present invention may also be formulated into liquid pharmaceutical compositions or medicaments, which are sterile solutions or suspensions that can be administered by, for example, intravenous, intraarterial, intramuscular, subcutaneous, intrathecal, intraperitoneal, or intra-cerebella injection.

The pharmaceutical composition or medicament of the present disclosure may be formulated as a solution suitable for parenteral administration, such as administration by injection, which includes, but is not limited to, subcutaneous, bolus injection, intramuscular, intraperitoneal and intravenous injection. The pharmaceutical composition or medicament of the present disclosure may alternatively be formulated as an isotonic suspension, solution or emulsion in oily or aqueous vehicles, and may contain one or more formulary agents, such as suspending, stabilizing and/or dispersing agents. Alternatively, the pharmaceutical composition or medicament of the present disclosure may be provided in dry forms, such as powders, crystallines or freeze-dried solids with sterile pyrogen-free water or isotonic saline before use. They may be presented in sterile ampoules or vials.

When the present mAb or the antibody fragment is formulated to be administered by intravenous, cutaneous or subcutaneous injection, the mAb will be in the form of a pyrogen-free, parenterally acceptable aqueous solution. The preparation of such parenterally acceptable polypeptide solutions, having due regard to pH, isotonicity, stability, and the like, is within the skill in the art. A preferred pharmaceutical composition or medicament for intravenous, cutaneous, or subcutaneous injection should contain, in addition to the present mAb or the antibody fragment, an isotonic vehicle, such as sodium chloride solution, Ringer's solution, dextrose solution, dextrose and sodium chloride solution, lactated Ringer's solution, or other vehicle as known in the art. The pharmaceutical composition or medicament of the invention may also contain stabilizer, preservative, buffer, antioxidant, or other additives known to those of skill in the art. The duration of intravenous therapy using the pharmaceutical composition or medicament of the invention will vary, depending on the severity of the disease being treated and the condition and potential idiosyncratic response of each individual subject. It is contemplated that the duration of each application of the present mAb will be in the range of 12 to 24 hours of continuous intravenous administration. Ultimately the attending physician will decide on the appropriate duration of intravenous therapy.

Another aspect of the present disclosure pertains to a method of treating a neurodegenerative disease in a subject in need thereof, such as a subject having or suspected of having a neurodegenerative disease, or a subject at risk of having a neurodegenerative disease. The method comprises administering to the subject an effective amount of the present antibody or a fragment thereof; or a pharmaceutical composition, or a medicament comprising the same.

The effective dose administered to the subject is from about 0.01 to 1,000 mg/Kg body weight of the subject, such as 0.01, 0.02, 0.03, 0.04, 0.05, 0.06, 0.07, 0.08, 0.09, 0.1, 0.2, 0.3 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 150, 200, 250, 300, 350, 400, 450, 500, 550, 600, 650, 700, 750, 800, 850, 900, 950, or 1,000 mg/Kg body weight of the subject; preferably, about 0.1 to 100 mg/Kg body weight of the subject. The dose can be administered in a single aliquot, or alternatively in more than one aliquot. A skilled artisan or clinical practitioner may adjust the dosage or regime in accordance with the physical condition of the patient or the severity of the diseases.

Examples of neurodegenerative diseases treatable by the present mAb, antibody fragment, medicament, pharmaceutical composition, and/or method include, but are not limited to, amyotrophic lateral sclerosis (ALS), Parkinson's disease (PD), Alzheimer's disease (AD), Huntington's disease (HD), frontotemporal dementia (FTD), spinocerebellar ataxias (SCA), Machado-Joseph disease (MJD), dentatorubral pallidoluysian atrophy (DRPLA), spinal and bulbar muscular atrophy (SBMA), fragile X-associated tremor and ataxia syndrome (FXTAS), and other diseases or disorders associated with and/or caused by neurotoxic peptides (such as Lewy body dementia (LBD)). In preferred embodiments, the neurodegenerative disease is AD.

Basically, the subject treatable by the present antibody or a fragment thereof, medicament, pharmaceutical composition, and/or method is a mammal, for example, human, mouse, rat, guinea pig, hamster, monkey, swine, dog, cat, horse, sheep, goat, cow, and rabbit. Preferably, the subject is a human.

The present mAb, antibody fragment, medicament, and/or pharmaceutical composition may be administered to the subject by a route selected from the group consisting of oral, enteral, nasal, transmucosal, and parenteral administration, in which the parental administration is any of intramuscular, intravenous, or intraperitoneal injection.

As would be appreciated, the present method can be applied to the subject, alone or in combination with additional therapies that have some beneficial effects on the prevention or treatment of neurodegenerative diseases. Depending on the intended or therapeutic purpose, the present method can be applied to the subject before, during, or after the administration of the additional therapies.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLES

Materials and Methods
Preparation of Human $CD14^+$ Monocytes

Peripheral blood mononuclear cells (PBMCs) were isolated from the whole blood of healthy human donors by standard density-gradient centrifugation. Then, $CD14^+$ cells were purified from PBMCs by high-gradient magnetic sorting with anti-CD14 microbeads.
Phagocytosis Assay of Latex Beads To test the short-term effect of anti-human Siglec-3 mAb, human $CD14^+$ monocytes ($5 \times 10^5$ in 100 µl) were pre-incubated with anti-Siglec-3 mAb (clone 1008) at 37° C. for 1 hour, followed by incubation with green fluorescent latex beads (final concentration: 0.025% or 0.005%) at 37° C. for 1 hour. Samples were washed once with PBS, and fixed by 4% paraformaldehyde on ice. 30 min later, the samples were washed once with PBS before permeabilization using 0.5% TRITON™ X-100 at room temperature for 15 minutes. The level of phagocytosis was measured by flow cytometry, and presented as mean fluorescence intensity (WI).

To test the long-term effect of anti-human Siglec-3 mAb, human $CD14^+$ monocytes ($5 \times 10^5$ in 100 µl) were pre-incubated with anti-Siglec-3 mAb (clone 1008) at 37° C. for 24 hours, followed by incubation with green fluorescent latex beads (final concentration: 0.025% or 0.005%) at 37° C. for 1 hour. Samples were washed once with PBS and fixed by 4% paraformaldehyde on ice for 30 min. The samples were then washed once with PBS before permeabilization using 0.5% TRITON™ X-100 at room temperature for 15 minutes. The level of phagocytosis was measured by flow cytometry and presented as WI.
Phagocytosis Assay of Amyloid $\beta_{1-42}$ To test the short-term effect of anti-human Siglec-3 mAb, human $CD14^+$ monocytes ($5 \times 10^5$ in 100 µl) were pre-incubated with anti-Siglec-3 mAb (clone 1008) at 37° C. for 1 hour, followed by incubation with green fluorescent amyloid $\beta_{1-42}$ oligomer (final concentration: 5 or 20 µg/ml) at 37° C. for another hour. Samples were washed once with PBS and fixed by 4% paraformaldehyde on ice. 30 minutes later, the samples were washed once with PBS before permeabilization by 0.5% TRITON™ X-100 at room temperature for 15 minutes. The level of phagocytosis was measured by flow cytometry and presented as MFI.

To test the long-term effect of anti-human Siglec-3 mAb, human $CD14^+$ monocytes ($5 \times 10^5$ in 100 µl) were pre-incubated with anti-Siglec-3 mAb (clone 1008) at 37° C. for 24 hours, followed by incubation with green fluorescent amyloid $\beta_{1-42}$ oligomer (final concentration: 5 or 20 µg/ml) at 37° C. for 1 hour. Samples were washed once with PBS and fixed in 4% paraformaldehyde on ice for 30 min. The samples were then washed once with PBS before permeabilization using 0.5% TRITON™ X-100 at room temperature for 15 minutes. The level of phagocytosis was measured by flow cytometry and presented as MFI.
Flow Cytometry Analysis Human $CD14^+$ monocytes were incubated with anti-Siglec-3 mAb (clone 1008; 3 µg/ml) or anti-PD-1 mAb (3 µg/ml) at 37° C. for 24 hours. After staining with anti-Silgec-3, anti-CD80, anti-CD86, and anti-MEC II antibodies, the cells were subjected to flow cytometry so as to determine whether the treatment of anti-Siglec-3 mAb would affect the expression level of Silgec-3, CD80, and CD86 on human $CD14^+$ monocytes.
Statistical Analysis Values are expressed as mean±standard deviation. All experiments repeated at least 3 times. The results were evaluated by Student t test. P value of 0.05 was regarded as significant.

Figure 1:
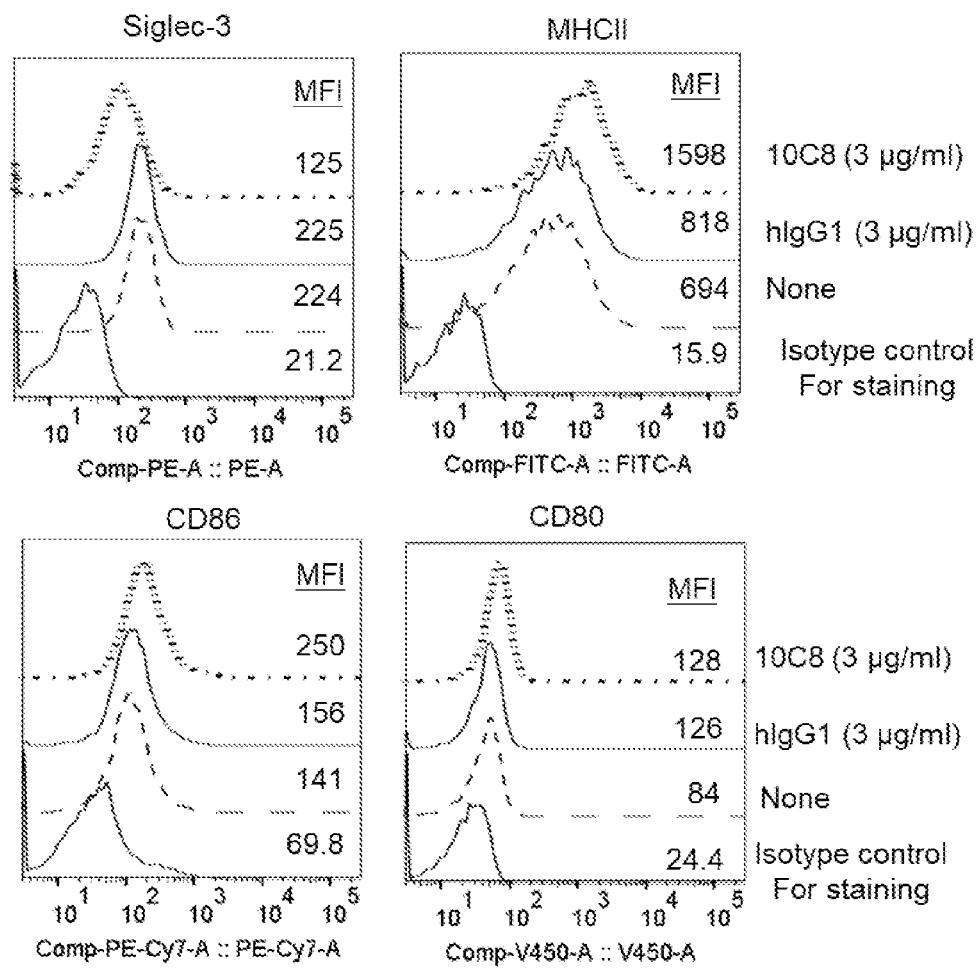
FIG. 1 depicts the results of flow cytometry according to Example 1.1 of the present disclosure, in which human $CD14^+$ monocytes were administered with specified treatment followed by the analysis of flow cytometry. None.

Example 1 Effect of mAb 1008 on Human $CD14^+$ Monocytes 1.1 Expression Level of Cellular Makers To verify whether the present mAb (i.e., mAb 1008) would affect the expression level of Siglec-3, CD80, CD86 and MEC II on monocytes, human $CD14^+$ monocytes treated with mAb 1008 were stained by anti-Siglec-3, anti-CD80, anti-CD86 and anti-MEC II antibodies followed by flow cytometry analysis. The result depicted in FIG. 1 confirmed that mAb 1008 down-regulated the expression level of Siglec-3, and up-regulated the respective levels of CD86 and MEW II. Regarding CD80, its expression level was not affected by the treatment of mAb 1008 (FIG. 1).
1.2 Phagocytic Analysis For the purpose of evaluating the effect of mAb 1008 on phagocytic activity of monocytes, human $CD14^+$ monocytes were incubated with mAb 1008 for 1 hour (short-term test, FIG. 2A) or 24 hours (long-term test, FIG. 2B), and then mixed with specific antigen (i.e., green fluorescent latex beads or amyloid $\beta_{1-42}$ oligomer) as described in Materials and Methods. The results were respectively depicted in FIGS. 2 and 3.

Compared with hIgG1 control group, mAb 1008 dose-dependently increased the uptake of latex beads by monocytes in both the short-term (FIG. 2A) and long-term (FIG. 2B) tests. The data of FIGS. 3A and 3B further confirmed the enhancement effect of mAb 1008, in which the treatment of mAb 1008 increased the level of amyloid $\beta_{1-42}$ oligomer uptaken by monocytes as compared to the IgG-treated group.

These results demonstrated that mAb 1008 was useful in removing neurotoxic peptide (i.e., amyloid $\beta_{1-42}$ peptide) by enhancing cellular phagocytosis, and accordingly, providing a potential means to treat neurotoxic peptide-related diseases, for example, neurodegenerative diseases (e.g., AD).

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method of treating a neurodegenerative disease in a subject, comprising administering to the subject an effective amount of an antibody via intrathecal or intra-cerebellar injection thereby ameliorating and/or alleviating the symptom associated with the neurodegenerative disease, wherein the antibody comprises, a light chain variable region comprising the amino acid sequences of VYY, ISSAG (SEQ ID NO: 1) and QYFNFP (SEQ ID NO: 2); and a heavy chain variable region comprising the amino acid sequences of NNGW (SEQ ID NO: 3), GIGPYGGSTF (SEQ ID NO: 4), and SRFIGSYSHM (SEQ ID NO: 5).

2. The method of claim 1, wherein the light chain variable region comprises the amino acid sequence at least 85% identical to SEQ ID NO: 6, and the heavy chain variable region comprises the amino acid sequence at least 85% identical to SEQ ID NO: 7.

3. The method of claim 2, wherein the light chain variable region comprises the amino acid sequence 100% identical to SEQ ID NO: 6, and the heavy chain variable region comprises the amino acid sequence 100% identical to SEQ ID NO: 7.

4. The method of claim 1, wherein the neurodegenerative disease is amyotrophic lateral sclerosis (ALS), Parkinson's disease (PD), Alzheimer's disease (AD), Huntington's disease (HD), frontotemporal dementia (FTD), spinocerebellar ataxias (SCA), Machado-Joseph disease (MJD), dentatorubral pallidoluysian atrophy (DRPLA), spinal and bulbar muscular atrophy (SBMA), or fragile X-associated tremor and ataxia syndrome (FXTAS).

* * * * *